United States Patent
He (10) Patent No.: US 10,444,169 B2
(45) Date of Patent: Oct. 15, 2019

(54) TWO-DIMENSIONAL X-RAY DETECTOR POSITION CALIBRATION AND CORRECTION WITH DIFFRACTION PATTERN

(71) Applicant: Bruker AXS, Inc., Madison, WI (US)

(72) Inventor: Bob Baoping He, Hercules, CA (US)

( * ) Notice: Subject to any disclaimer, the term of this patent is extended or adjusted under 35 U.S.C. 154(b) by 374 days.

(21) Appl. No.: 15/162,889

(22) Filed: May 24, 2016

(65) Prior Publication Data

US 2017/0343490 A1    Nov. 30, 2017

(51) Int. Cl.
*G01N 23/207*  (2018.01)
*G01N 33/00*  (2006.01)

(52) U.S. Cl.
CPC ... *G01N 23/207* (2013.01); *G01N 2033/0091* (2013.01); *G01N 2223/0566* (2013.01); *G01N 2223/303* (2013.01); *G01N 2223/32* (2013.01); *G01N 2223/501* (2013.01)

(58) Field of Classification Search
CPC ..... G01N 2223/0566; G01N 2223/303; G01N 23/207; G01N 2033/0091; G01N 2223/32; G01N 2223/501
See application file for complete search history.

(56) References Cited

U.S. PATENT DOCUMENTS

2012/0014508 A1*  1/2012  Wormington ........ G01N 23/207
378/71

OTHER PUBLICATIONS

He, Bob B., Two-Dimensional X-Ray Diffraction, (2009), John Wiley & Sons, Inc., pp. 163-167. (Year: 2009).*

* cited by examiner

*Primary Examiner* — Chih-Cheng Kao
(74) *Attorney, Agent, or Firm* — Benoit & Côté Inc.

(57) ABSTRACT

A method of determining the spatial orientation of a two-dimensional detector in an X-ray diffractometry system, and calibrating the detector position in response thereto, uses diffraction patterns from a powder sample collected at a plurality of detector swing angles. The overlapping of the detected patterns indicates relative errors in the detector orientation. In particular, intersection points between the different diffraction patterns may be located, and their relative locations may be used to identify errors. Such errors may be in the detector position, or they may be errors in different rotational directions, such as roll, pitch or yaw. Determination and correction of the detector orientation using this method may be part of a calibration routine for the diffractometry system. Roll error may also be determined using a single measurement with the detector at a swing angle perpendicular to the X-ray beam.

11 Claims, 8 Drawing Sheets

TWO-DIMENSIONAL X-RAY DETECTOR POSITION CALIBRATION AND CORRECTION WITH DIFFRACTION PATTERN

BACKGROUND OF THE INVENTION

Field of the Invention

This invention relates generally to the field of X-ray diffraction and, more specifically, to the position calibration of a two-dimensional X-ray detector.

Description of the Related Art

Figure 1:
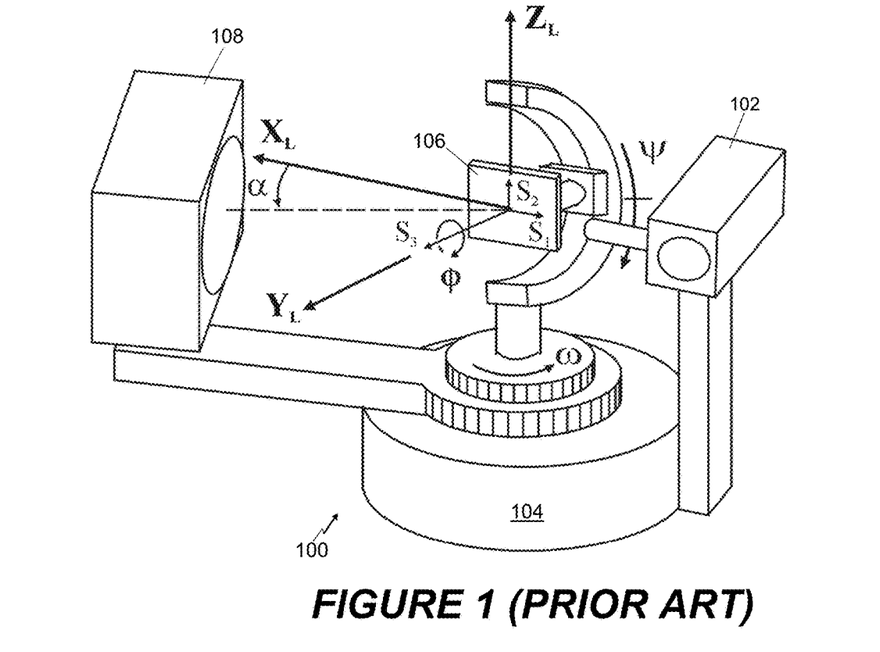
FIG. 1 is a schematic view of an X-ray diffractometry system as known in the art.

A typical laboratory system 100 for performing X-ray diffraction experiments consists of several components as shown in FIG. 1. The components include an X-ray source 102 (with associated optics) that produces a primary X-ray beam with the required radiation energy, focal spot size and intensity. A goniometer 104 is used to establish and manipulate geometric relationships between the incident X-ray beam, a sample 106 located at the goniometer center and a two-dimensional (2D) X-ray detector 108. The incident X-ray beam illuminates the sample 106 and produces scattered X-rays which are recorded by the detector 108.

The configuration of FIG. 1 is known as a horizontal diffractometer, as the rotation angle ω of the sample and the rotation angle α of the detector are in a horizontal plane relative to ground level. The system also has "left-hand" orientation, as the goniometer 100 is mounted in the left side of the x-ray tube and primary optics 102 as observed by the operator. The diffractometer plane is determined by the direction of the primary x-ray beam, which follows the $X_L$ axis and which, in this configuration, is fixed. The change in the ω angle is achieved by sample rotation and the α angle is achieved by detector rotation independently.

Figure 2:
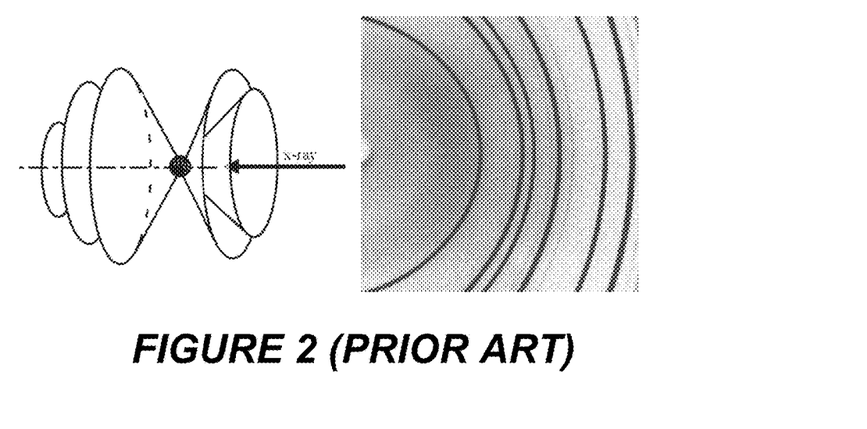
FIG. 2 is a schematic view of the diffraction cones of a diffractometry system like that of FIG. 1, and a resulting pattern of diffraction rings detected by the detector.

During operation of a system like that of FIG. 1, knowing the accurate position and orientation of the detector 108 in the diffractometer is crucial for determining a precise X-ray scattering angle from a sample and collecting a correct 2D diffraction pattern. For example, when examining a polycrystalline (powder) sample, a series of diffraction cones are produced by the large number of crystals randomly oriented in the sample, each diffraction cone corresponding to diffraction from the same family of crystalline planes. This is shown in FIG. 2, on the left side of which is a schematic view of how the scattered X-rays emanate from the sample, while the right side of the figure shows a typical set of diffraction rings detected by a 2D detector. Since the orientations of the diffraction cones are solely determined by the orientation of the incident X-ray beam, knowing the precise position of detector is necessary for proper measurement of the diffraction cones and identification of the sample.

SUMMARY OF THE INVENTION

In accordance with the present invention, a method is providing for determining the spatial orientation of a two-dimensional detector in an X-ray diffractometry system used for detecting X-ray energy diffracted from a sample at a sample location. This determination may be part of a calibration process for properly orienting the detector prior to testing a sample, or may be used to compensate subsequent diffractometry measurements to correct for deviation of the detector spatial orientation from a desired orientation. In an exemplary embodiment of the invention, a polycrystalline material is located at the sample location, and an X-ray beam is directed toward the polycrystalline material such that diffracted X-ray energy is output therefrom. The detector is used to detect a first diffraction pattern formed by the diffracted X-ray energy with the detector positioned at a first swing angle defined between the direction of the X-ray beam and a line from a center of a detection surface of the detector to the sample. A second diffraction pattern is then detected with the detector positioned at a second swing angle different than the first swing angle, and the detected positions of the first and second diffraction patterns on the detection surface are compared and used to determine the spatial orientation of the detector.

This embodiment of the invention makes use of the fact that the relative positions of diffraction patterns collected at different detector swing angles may be indicative of misalignments of the detector. Depending on the particular misalignment in question, detection at two or more swing angles may be sufficient to identify them and may be used to indicate the correction needed to properly orient the detector as part of initial calibration or to compensate the subsequently detected diffraction data. In particular, the method may involve locating points of intersection between the rings of diffraction patterns collected at different swing angles, and by comparing the relative positions of those intersection points to anticipated relative positions, the spatial orientation may be determined.

Examples of the detector misalignments that may be identified include an error in the roll angle, which is the rotational orientation of the detector about an axis between a center of the sample and a center of the detection surface of the detector. Another rotational orientation that may be determined is the pitch angle, which is rotation about an axis within the plane of a detection surface of the detector, typically a horizontal axis relative to the orientation of the diffractometry system. Similarly, a yaw angle may also be determined which represents rotation about another axis within the plane of the detection surface that is perpendicular to the pitch angle.

In an alternative embodiment, an angular orientation of the detector about the roll axis between a center of a detection surface of the detector and a center of a sample location may be determined using detection at a single swing angle. In this embodiment, a polycrystalline sample is located at the sample location and an X-ray beam is directed toward the sample along a first direction such that diffracted X-ray energy is output therefrom. The detector is positioned at a swing angle of 90° such that the roll axis is substantially perpendicular to the first direction. At this angle, a portion of the diffraction pattern from the sample that is in close proximity to the center of the detection surface will be substantially linear in a vertical direction relative to the orientation of the diffractometer. This substantially linear portion is detected with the detector and its orientation is identified relative to a pixel array of the detector. Deviation of the substantially linear portion from a vertical direction relative to the pixel array is thus indicative of a roll error.

In response to the detection of the relative position of the different diffraction angles, the detector may be repositioned to a desired orientation. Using an appropriate control system, the detection and analysis of the relative positions of the diffraction patterns and/or the intersection points may be automated and integrated into the calibration routine of diffractometry systems. Alternatively, the determined spatial orientation of the detector may be used to compensate subsequent diffractometry measurements for deviation of the spatial orientation from a desired orientation.

DETAILED DESCRIPTION

Figure 3:
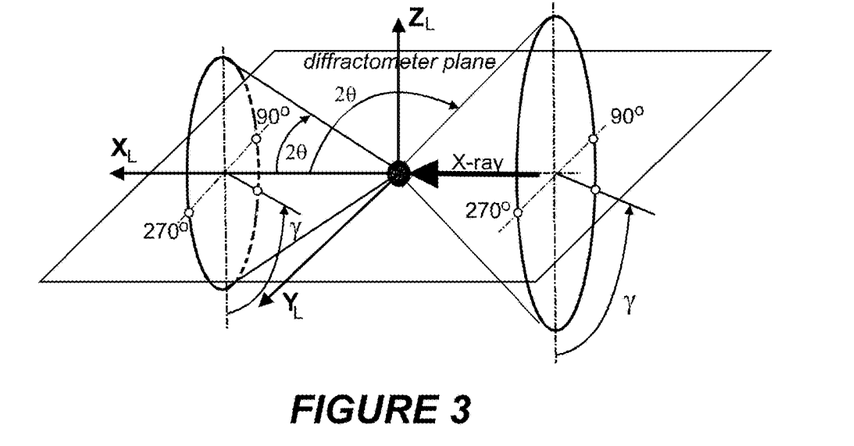
FIG. 3 is a geometric diagram of a diffractometry system showing the laboratory coordinates associated therewith.

The schematic view of FIG. 3 describes the geometric definition of diffraction cones in the laboratory coordinates system, $X_L Y_L Z_L$. The origin of the coordinates is also called the goniometer center or instrument center. The direct x-ray beam propagates along the $X_L$ axis, which is also the rotation axis of the diffraction cones. The apex angles of the cones are determined by the $2\theta$ values given by the Bragg equation:

$$n\lambda = 2d \sin \lambda \qquad (2)$$

where $\lambda$ is wavelength, d is the distance between adjacent crystal planes (d-spacing), $\theta$ is the Bragg angle at which one observes a diffraction peak, and n is a integer number, known as the order of reflection.

As shown in FIG. 3, the apex angles of the diffraction cones are twice the $2\theta$ values for forward reflection ($2\theta \geq 90°$) and twice the values of $180°-2\theta$ for backward reflection ($2\theta > 90°$). The $X_L$-$Y_L$ plane is the diffractometer plane, and the $\gamma$ angle is the azimuthal angle about the $X_L$ axis having an origin at the intersection of a diffraction cone and an axis parallel to the $-Z_L$ direction. The $\gamma$ angle may therefore be used to define the direction of a diffracted beam of the cone. The conventional diffractometer plane corresponds to $\gamma=90°$ in the negative $Y_L$ direction and $\gamma=270°$ in the positive $Y_L$ direction. The $\gamma$ and $2\theta$ angles together form a spherical coordinate system that can be used to describe all directions from the origin of the sample (i.e., the goniometer center). The $\gamma$-$2\theta$ system is fixed in the laboratory coordinate system $X_L Y_L Z_L$, which is independent of the sample orientation in the goniometer.

Figure 4:
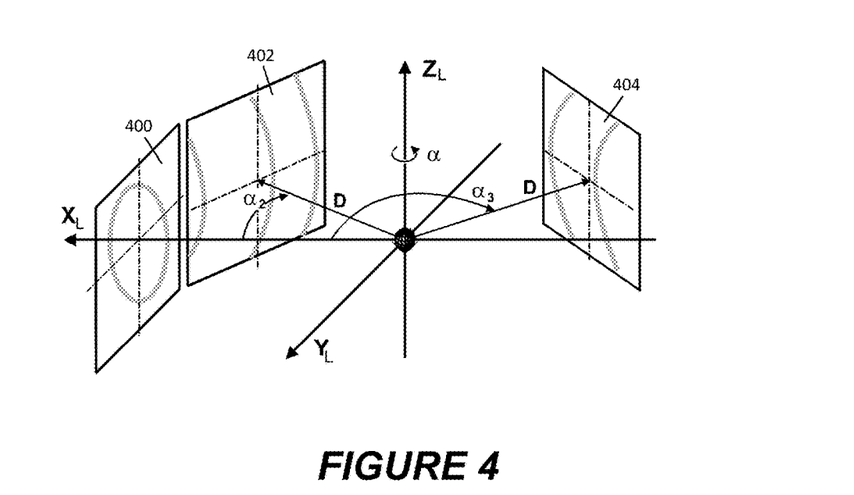
FIG. 4 is a schematic diagram showing the rings of a diffraction pattern collected by the detector at a plurality of different swing angles.

A flat 2D detector is shown schematically in FIG. 4 at several different positions relative to laboratory coordinates $X_L Y_L Z_L$. The detection surface can be considered as a plane, which intersects a diffraction cone emitted from the sample to form a conic section. The detector position is defined by the sample-to-detector distance D and the detector swing angle $\alpha$, which is measured relative to the positive $X_L$ axis. D is the perpendicular distance from the goniometer center to the detection plane and a is a right-handed rotation angle about the $Z_L$ axis. At position 400 shown in the figure, the center of the detector is at the $X_L$ axis, with $\alpha=0$. At detector positions 402 and 404, the detector is rotated away from the $X_L$ axis with swing angles $\alpha_2$ and $\alpha_3$, respectively, each of which is a negative swing angle. At a given swing angle $\alpha$, a range of $2\theta$ values can be measured by a 2D detector.

To analyze X-ray diffraction data, it is necessary to find the diffraction space coordinates ($2\theta$, $\gamma$) of each pixel in the 2D detector. The calculation is based on the detector space parameters and the pixel position in the detector. Within the plane of the detector, the position of a pixel is defined by coordinates (x, y), where the detector center is defined as x=y=0. The detector center and accurate coordinates for each pixel are determined by specific detector design, calibration and spatial correction. The $2\theta$ and $\gamma$ values of a point P(x,y) on a flat 2D detector are given by:

$$2\theta = \arccos \frac{x\sin\alpha + D\cos\alpha}{\sqrt{D^2 + x^2 + y^2}}, \; (0 < 2\theta < \pi) \qquad (3)$$

$$\gamma = \frac{x\cos\alpha - D\sin\alpha}{|x\cos\alpha - D\sin\alpha|} \arccos \frac{-y}{\sqrt{y^2 + (x\cos\alpha - D\sin\alpha)^2}}, \qquad (4)$$

$$(-\pi < \gamma \leq \pi)$$

The inverse functions for these expressions can also be determined, such that coordinates (x, y) may be represented in terms of coordinates (($2\theta$, $\gamma$) as follows:

$$x = \frac{\cos\alpha \tan 2\theta \sin\gamma + \sin\alpha}{\cos\alpha - \sin\alpha \tan 2\theta \sin\gamma} D, \; (-\pi \leq \alpha \leq \pi, \; 0 \leq 2\theta < \pi) \qquad (5)$$

$$y = -(x\sin\alpha + D\cos\alpha)\tan 2\theta \cos\gamma \; (-\pi \leq \alpha \leq \pi, \; 0 \leq 2\theta < \pi) \qquad (6)$$

The detector position in the laboratory coordinates must be determined in order to analyze a diffraction pattern with accuracy. In a diffractometer such as that shown in FIG. 1, D can be changed manually or automatically with a motorized stage and a can be changed automatically by the goniometer. Since a typical goniometer has very high precision and accuracy, an accurate a is ensured, and no additional attention is needed from users. However, accurate values of the sample-to-detector distance D and the beam center ($x_c$, $y_c$) on the detector surface must be calibrated at each nominal distance D.

Figure 5:
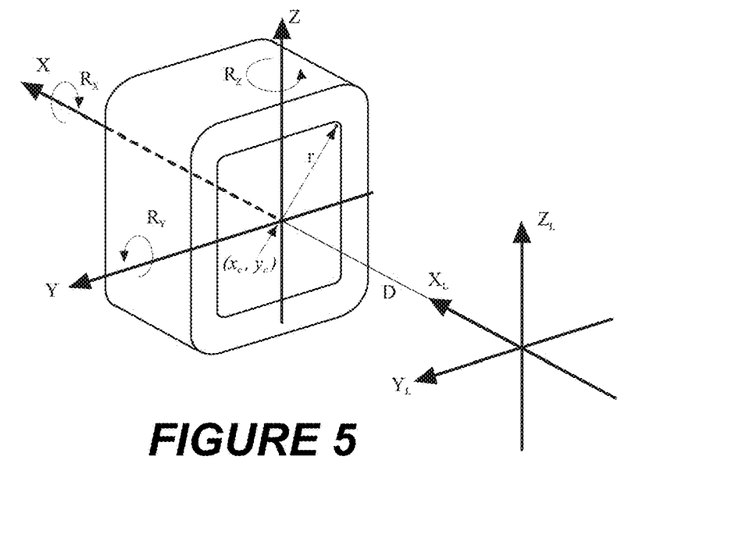
FIG. 5 is a schematic diagram of the detector of a diffractometry system showing the coordinates used in the detector space.

An accurate detector position in a diffractometer is first determined by the mechanical mount, adjustment and motorized driving stages. FIG. 5 shows the position of a detector in the laboratory coordinates, $X_L Y_L Z_L$, with the detector located at on-axis position $\alpha=0$. The intersection of the detector plane with the $X_L$ axis is the beam center on the detector. New coordinates XYZ can be created with a parallel translation of $X_L Y_L Z_L$ in the $X_L$ direction by the sample-to-detector distance D. The Y and Z axes are within the detector plane. In order to maintain consistency, the detector pixel position within the detector is given by the x, y coordinates. At this particular detector position ($\alpha=0$), the x, y coordinates are located in the plane formed by the Y and Z axes. The accuracy of the detector position is determined by six tolerance parameters in three translations (X,Y,Z) and three rotations ($R_X$, $R_Y$, $R_Z$). The rotations, $R_X$, $R_Y$, and $R_Z$ are the rotations about the three axes, X, Y, and Z, and are referred to, respectively, as roll, pitch and yaw. Misalignments of the detector in any of the translation directions or rotation angles manifest themselves in the detector plane as a shift of the measured diffraction spots. The criterion of the tolerance is the amount of the pixel shift produced by these errors. An error along the X axis corresponds to an error in the sample-to-detector distance D. Translation errors along the Y and Z axes produce pixel shifts of the same magnitude within the detector plane, while pixel shifts caused by errors in the three rotational directions vary as a function of the amount of the rotation error and the distance between the pixel and the center of the detector surface. The maximum shift occurs at the pixels farthest from the detector center. The pixel shift on the detector plane due to an error in X depends on the sample-to-detector distance D and the distance from the pixel in question to the center of the detector surface.

The descriptions of the six tolerance parameters and the corresponding equations for calculating the pixel shift that results from errors are summarized in Table 1. The errors corresponding to X, Y, Z, $R_X$, $R_Y$, and $R_Z$ are denoted as $\Delta X$, $\Delta Y$, $\Delta Z$, $\Delta R_X$, $\Delta R_Y$, and $\Delta R_Z$, respectively. The shift tolerance can be as large as several pixels since the errors can be corrected by detector calibration. The three translation errors $\Delta X$, $\Delta Y$ and $\Delta Z$ can be corrected by the calibration of the detector distance and beam center, so those tolerances can be relatively large. The errors $\Delta R_X$, $\Delta R_Y$, and $\Delta R_Z$ can only be partially compensated by correction and calibration so the tolerance tends to be more critical. Various detector distances are used for different applications. The shift caused by the errors $\Delta X$, $\Delta R_X$, $\Delta R_Y$, and $\Delta R_Z$ increase with increasing distance r from the detector center and decreasing D, so the tolerance must be given for the largest pixel-to-center distance ($r_{max}$) and shortest detector distance ($D_{min}$). Detector correction and calibration values at several detector distances are normally collected and saved. The values are reused when the corresponding detector distance is used. Therefore, the pixel shift caused by the reproducibility errors cannot be further corrected, and must be kept to a minimum. The tolerance and reproducibility should be decided based on the detector type and the application requirements. In addition to the equations for calculating the pixel shift caused by each error, Table 1 also gives examples of the tolerance and reproducibility for an 11 cm round detector. The tolerance is given based on a pixel shift of approximately three pixels and the reproducibility is based on a pixel shift of one pixel.

TABLE 1

| | | | $D_{min}$ = 60 mm, $r_{max}$ = 55 mm, pixel size = 0.11 mm | |
|---|---|---|---|---|
| Axis | Description | Equation for shift in detector plane | Tolerance 0.35 mm | Reproducibility 0.11 mm |
| X | Detector distance | $(r/D) \cdot \Delta X$ | 0.38 mm | 0.12 mm |
| Y | Horizontal | $\Delta Y$ | 0.35 mm | 0.11 mm |
| Z | Vertical | $\Delta Z$ | 0.35 mm | 0.11 mm |
| $R_x$ | Roll | $r \cdot \sin(\Delta R_x)$ | 0.37° | 0.12° |
| $R_y$ | Pitch | $(r^2/D) \cdot \sin(\Delta R_y)$ | 0.40° | 0.13° |
| $R_z$ | Yaw | $(r^2/D) \cdot \sin(\Delta R_z)$ | 0.40° | 0.13° |

The detector position calibration determines the detector distance (D), swing angle (a), and beam center ($x_c$, $y_c$). The appropriate calibration permits accurate calculation of $2\theta$ and $\gamma$ values of pixels and diffraction features if the errors about three rotations ($R_X$, $R_Y$, $R_Z$) are zero or within the tolerance. The precise detector distance, swing angle and beam center are determined by taking diffraction frames of a known standard and comparing the measured diffraction rings with the calculated rings from the known peak $2\theta$ positions and detector position. Any polycrystalline or powder exhibiting high stability and sharp diffraction lines, such as corundum, quartz, or silicon, can be used as a calibration standard. The calibration can be done manually by overlapping the calculated rings with the measured diffraction frame. By adjusting the values of detector distance, swing angles and beam center, the calibrated values are found when the best correspondence between the calculated and measured rings occurs.

Figure 6:
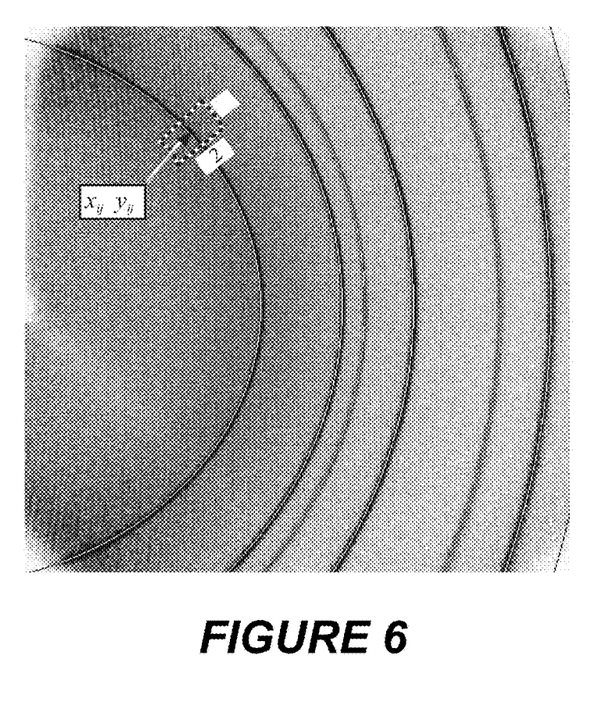
FIG. 6 is a diagram showing the detected diffraction rings of a corundum powder sample relative to the anticipated location of those rings.

FIG. 6 shows the diffraction frame collected from a corundum (NIST SRM 676 $\alpha$-$Al_2O_3$) powder sample with a two-dimensional diffraction system (the GADDS™ General Area Detector Diffraction System, Bruker AXS, Inc., Madison, Wis.). The software displays the diffraction frame and the calculated diffraction rings (shown as white lines in the figure) based on the standard d/I file (PDF card 46-1212). The detector distance, swing angle and beam center can be adjusted interactively by mouse or arrow keys until all the calculated rings are precisely centered over the collected diffraction rings in the data frame. In a short $2\theta$ range, the positions of the same sets of calculated rings may be moved by either changing the swing angle or beam center (particularly $x_c$) to generate almost the same effect. In this case, the error in swing angle may be compensated by an error in beam center. This is referred to as the coupling effect between the detector position parameters. In order to get a precise calibration and overcome the coupling effect, it is desirable to collect several frames at different swing angles. The sensitivity of the calibration to each parameter varies with the swing angle. For example, the diffraction frames collected at a low swing angle or on-axis position have better sensitivity to the beam center, while the frames collected at a large swing angle are more sensitive to the detector distance. The swing angle and beam center calibration can be decoupled if the frames are collected at both positive and negative swing angles.

The swing angle ($\alpha$) may be determined independently by collecting a direct beam image with appropriate attenuation at more than two detector distances, preferably at the shortest and longest detector distances. For non-zero swing angles, the image of the beam will be represented by a spot having a location on the detection surface (in the x,y detector coordinates) that changes as the distance D of the detector from the sample changes. Similarly, the swing angle α=0 is determined when the direct beam images are close to the center of the detection surface, and the measured position of the beam center ($x_c$, $y_c$) is the same at all detector distances. The swing angles at other values are guaranteed by the goniometer, which typically has accuracy better than 0.01 degrees and reproducibility better than 0.001 degrees. In this case, only the detector distance and the beam center need to be calibrated using the predetermined swing angle.

The calibration can also be done automatically by a computer program. The locations of the diffraction rings in the calibration frames are first determined in each section as shown in FIG. 6 as the dotted line box. The α2θ and Δγ is first determined based on an initial approximation of detector distance, swing angle and beam center. The gravity center of the intensity distribution of the section is then calculated as $x_{ij}$ and $y_{ij}$. For the sharp peaks and negligible preferred orientation from the calibration sample, the coordinates $x_{ij}$ and $y_{ij}$ represents the $i^{th}$ point on the $j^{th}$ diffraction ring. The residual for this point on the diffraction ring is given as:

$$r_{ij} = 2\theta_j - \cos^{-1} \frac{(x_{ij} - x_c)\sin\alpha + D\cos\alpha}{\sqrt{D^2 + (x_{ij} - x_c)^2 + (y_{ij} - y_c)^2}} \quad (7)$$

where $2\theta_j$ is the Bragg angle of the $j^{th}$ diffraction ring from the standard reference material. The summed square of residuals is given as:

$$S = \sum_{j=1}^{n}\sum_{i=1}^{m_j} r_{ij}^2 = \sum_{j=1}^{n}\sum_{i=1}^{m_j}\left(2\theta_j - \cos^{-1}\frac{(x_{ij}-x_c)\sin\alpha + D\cos\alpha}{\sqrt{D^2+(x_{ij}-x_c)^2+(y_{ij}-y_c)^2}}\right)^2 \quad (8)$$

where $m_j$ is the number of data points on the $j^{th}$ diffraction ring and n is the total number of diffraction rings used for calibration from all frames. Three parameters, detector distance (D), swing angle (α), and beam center ($x_c$, $y_c$) are determined by a nonlinear least squares regression. There are many nonlinear least squares routines available to use. The typical regression step is to start with the initial estimated values and then adjust the parameters in a given region by iterations with gradually reduced steps until the summed square of residuals reaches a minimum. It must be noted that, in order to determine the calibrated beam center, arbitrary x,y origin coordinates are assumed.

Figure 7:
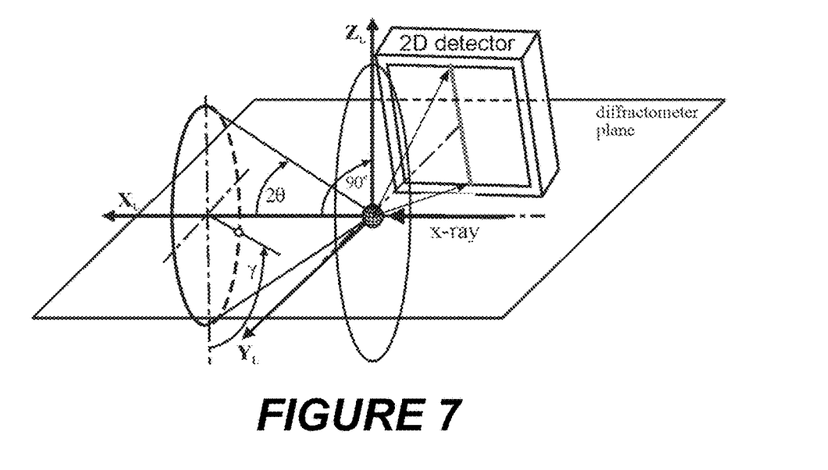
FIG. 7 is a schematic diagram of a detector positioned at a swing angle of approximately 90° and the corresponding straight line segment of a diffraction ring that is detected thereby.
Figure 8:
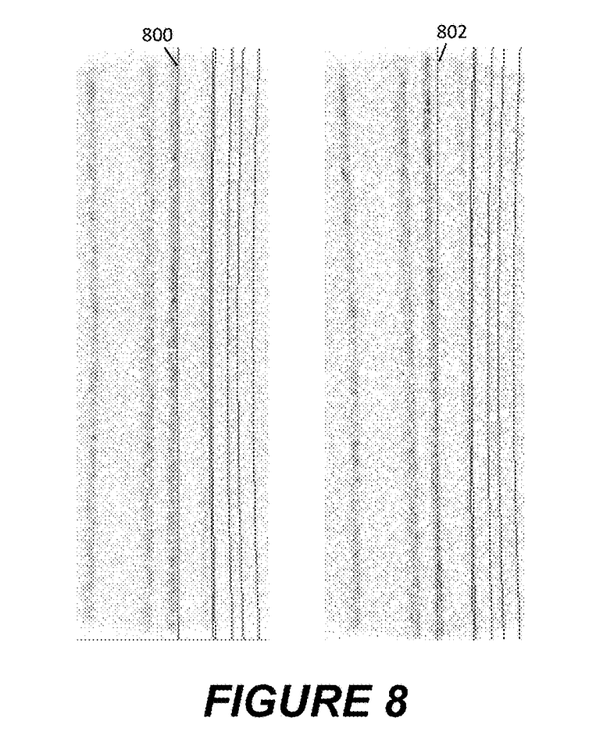
FIG. 8 is a diagram showing diffraction ring segments detected at an approximately 90° swing angle and the anticipated position of those lines indicating a roll error in the orientation of the detector.

If diffraction angle 2θ=90°, the diffraction cone becomes a plane perpendicular to the incident X-ray beams, as is shown in FIG. 7. The diffraction ring collected by a flat 2D detector becomes a vertical straight line. If there is no "roll" error, the straight diffraction ring should be parallel to the y-direction of the detector. Therefore, scattered x-rays along this ring will be detected by the pixels of the same x coordinates independent of y. By comparing the scattered intensity distribution and pixel array, the "roll" angle can be measured. In practice, the 2θ of the ring does not have to be exactly 90°, but only within a reasonable vicinity of 90°. FIG. 8 shows two frames collected from corundum at 2θ near 90°. The left is collected with a detector having little or no roll error and, as shown, the simulated diffraction ring (as indicated by the line 800) is almost parallel to the measured diffraction ring. The right frame is collected with a detector having a significant roll error. In this case, the simulated ring (as indicated by the line 802) forms an angle to the measured diffraction ring. The roll angle can be evaluated from the angle between the simulated ring and the ring fitted from the diffraction data.

Figure 9:
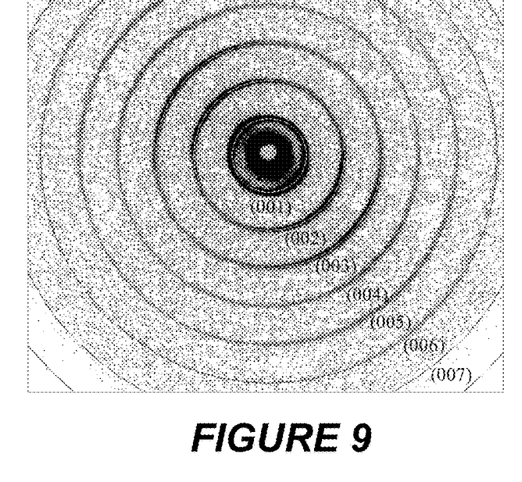
FIG. 9 is an image of the diffraction pattern detected from a silver behenate powder sample.

A series of diffraction cones can be produced from a polycrystalline (powder) sample. Each diffraction cone corresponds to the diffraction from the same family of crystalline planes in all the participating grains. If there is no strain (stress) or other defects causing the change of d-spacing, the diffraction cones are regular cones with constant 2θ for each cone. All diffraction cones share the same rotation axis which is also the trajectory of the incident X-ray beam. FIG. 9 shows a diffraction frame collected from silver behenate powder at a nominal detector distance of 30 cm. Due to the large d-spacing lattice plane ($d_{001}$=53.38 Å), a set of concentric and evenly spaced diffraction rings from (001) planes are observed and can be used to calibrate the detector distance and beam center. The 2θ values of all diffraction rings can be evaluated from d-spacing values of (001) planes, but the diffraction rings do not reveal the γ value of a particular scattering direction.

Figure 10:
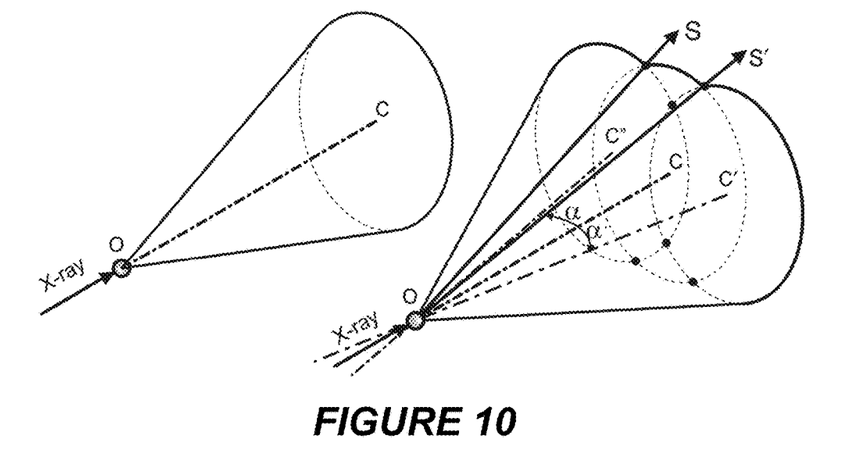
FIG. 10 is a schematic diagram showing the projection of different diffraction cones at different swing angles.

In one embodiment of the invention, the position of a 2D detector may be calibrated by observation of the overlap between diffraction cones that correspond to different scattering directions. Shown schematically in FIG. 10 is a single diffraction cone (along the left side of the figure), and a set of three overlapping diffraction cones (along the right side of the figure). In each case, the location of the sample is identified as position O. The lone diffraction cone shown along the left side of the figure represents the central cone of the three overlapping cones in the right side of the figure. The line O-C identifies the rotation axis of this diffraction cone, and follows the axis of the incident X-ray beam. The other two diffraction cones have different swing angles, α and α', relative to the central diffraction cone, which has a swing angle of zero. These different swing angles can be achieved by rotation of the incident X-ray beam about the sample (instrument center), rotation of the 2D detector about the sample, or rotation of both.

The overlapping diffraction cones have different rotation axes, as shown in the figure. Whereas the rotation axis of the central diffraction cone is represented by the line O-C, the rotation axes of the other two diffraction cones are identified as O-C' and O-C". Within a given plane, each of the diffraction rings formed by the cones intersects with the diffraction ring of another cone at two specific points. Since the three rings all mutually overlap, this creates a total of six intersection points that are uniquely identifiable within that plane, which are shown as black dots in the figure. Moreover, each of these points represents a unique scattering direction that is shared by the two cones that intersect at that point. For example, the lines O-S and O-S' shown in FIG. 10 represent two of these unique scattering directions. For a 2D detector that is positioned to detect the X-ray energy from each of the six scattering directions represented by the intersection of the cones, the relative location of these points within the detection plane of the detector can be used to calibrate the detector position.

Figure 11:
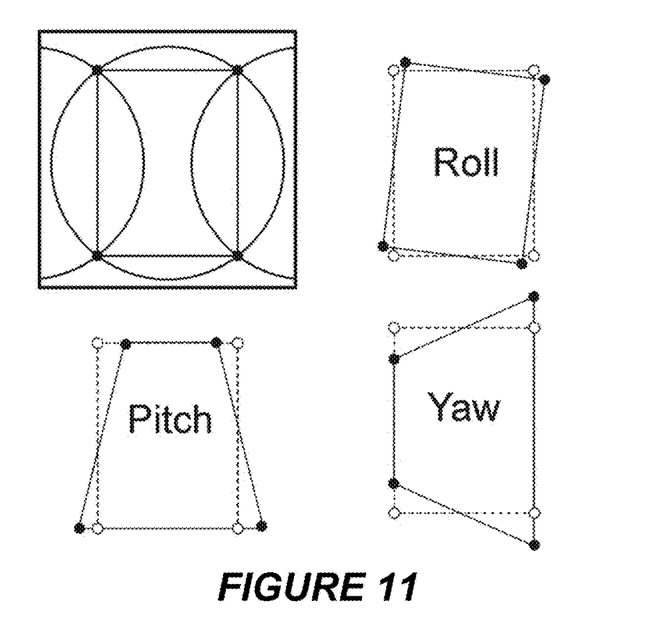
FIG. 11 is a schematic diagram showing the relationship between the relative locations of intersection points between diffraction patterns collected at different swing angles and corresponding detector orientation errors.

Calibration based on scattering angles determined from the intersections between diffraction rings can be done in different ways, and can be used to measure different types of errors. In addition to the detector distance and the location of the detector center, as described above, the detector orientation (i.e., rotation) errors, namely roll, pitch and yaw, can also be determined from the intersections. FIG. 11 illustrates the basic concept of this calibration. The upper-left of the figure shows four intersections (black dots) produced by overlapping three diffraction rings collected at equal swing angle steps. If the detector has no orientation error, a quadrilateral shape formed by lines connecting the four intersections is a rectangle that is rotationally aligned with the detector surface. However, this rectangle will distort in shape or orientation if there is an error in the detector orientation.

The upper-right portion of FIG. 11 illustrates the distortion produced by a "roll" error in the position of the detector. The dashed line rectangle shows the position of the quadrilateral shape formed by the intersections when there is no error, while the solid line shape indicates the detected position. The rotational misalignment of the detector about an axis perpendicular to the detection surface creates the resulting error, which is manifested in the rotational displacement of the detected intersection points. To calibrate the detector to compensate for this error, the detector or the collected images may be rotated about the perpendicular axis by the amount of the displacement error. If adjusting the detector, the adjustment is a physical change in the detector orientation, while rotation of the collected images is accomplished by adjustment of the data representing the images so as to counteract the effect of the error, in essence effectuating a "virtual" rotation of the collected images.

The bottom-left portion of FIG. 11 illustrates the distortion produced by a "pitch" error in the position of the detector. Again, the dashed line rectangle shows the position of the quadrilateral shape formed by the intersections when there is no error, while the solid line shape indicates the detected position. The rotational misalignment of the detector about a horizontal axis (relative to the orientation of the figure) creates the resulting error, which is manifested in a difference in the horizontal separation between the intersection points closer to the top of the detector relative to the separation of the points closer to the bottom of the detector. The distortion in the detected location of the intersection points results from the actual pixel-to-sample distances for the intersections not being symmetric about the detector center. To calibrate the detector to compensate for this error, the detector is rotated about the horizontal axis by the amount of the displacement error, or the collected image data is provided with a software correction, as discussed above.

The bottom-right portion of FIG. 11 shows illustrates the distortion produced by a "yaw" error in the position of the detector. Again, the dashed line rectangle shows the position of the quadrilateral shape formed by the intersections when there is no error, while the solid line shape indicates the detected position. The rotational misalignment of the detector about a vertical axis (relative to the orientation of the figure) creates the resulting error, which is manifested in a difference in the vertical separation between the intersection points closer to the left side of the detector relative to the separation of the points closer to the right side of the detector. As with the "pitch" error, the distortion in the detected location of the intersection points in this example results from the actual pixel-to-sample distances for the intersections not being symmetric about the detector center. To calibrate the detector to compensate for this error, the detector is rotated about the vertical axis by the amount of the displacement error, or the collected image data is provided with a software correction, as discussed above.

While FIG. 11 provides a relatively simple demonstration of the principles of the invention, it will be understood that the actual detector orientation error can be a combination of any or all of the three (roll, pitch and yaw). In addition, the number of intersection points used for the calibration can also much higher, so that the detector orientation error can be calculated more accurately, with proper fitting and regression to all the available reference points. In particular, the relative locations of intersection points across the detection surface may indicate not just degrees of errors in different lateral and rotational directions, but also the position of the rotational axes about which the rotational errors occur. A compensation routine making use of the relative intersection position information may be employed to reposition the detector so that the various errors are eliminated, or the collected image data may be provided with a software correction, as discussed above.

Figure 12:
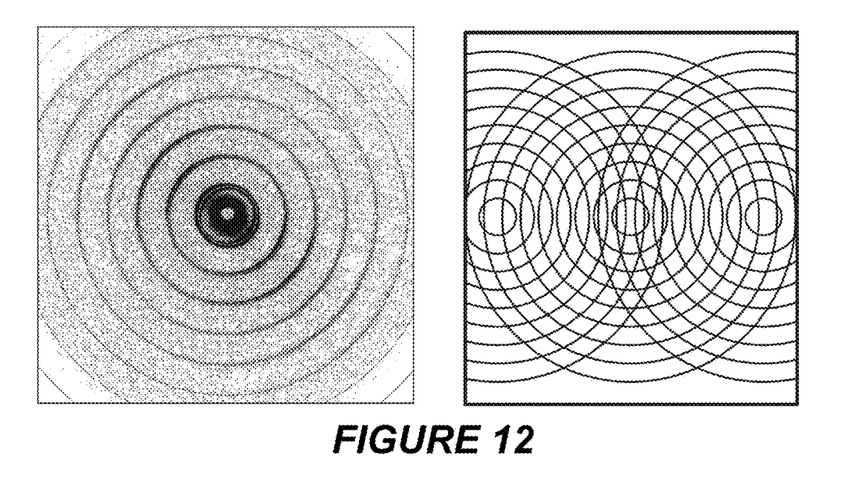
FIG. 12 shows the diffraction pattern collected from silver behenate and the expected overlapping of the rings of this diffraction pattern if taken at three different swing angles.
Figure 13:
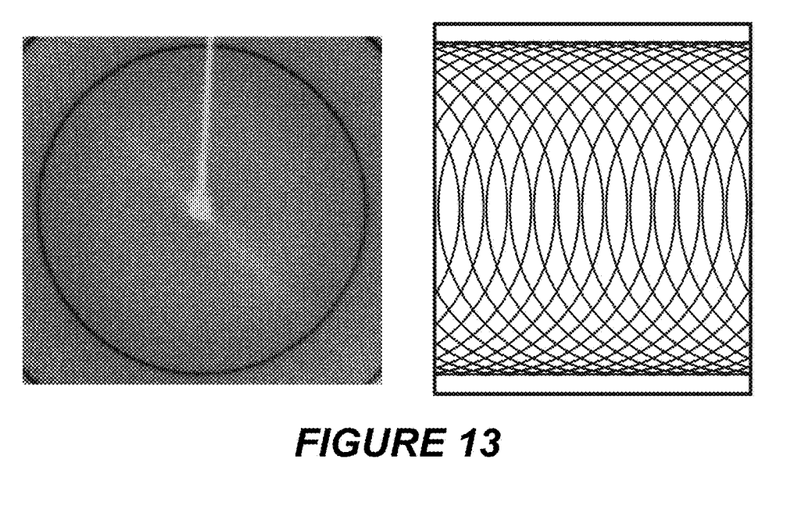
FIG. 13 shows a diffraction ring collected from a corundum powder sample and the expected overlapping of the rings of a corresponding diffraction pattern if taken at numerous swing angles.
Figure 14:
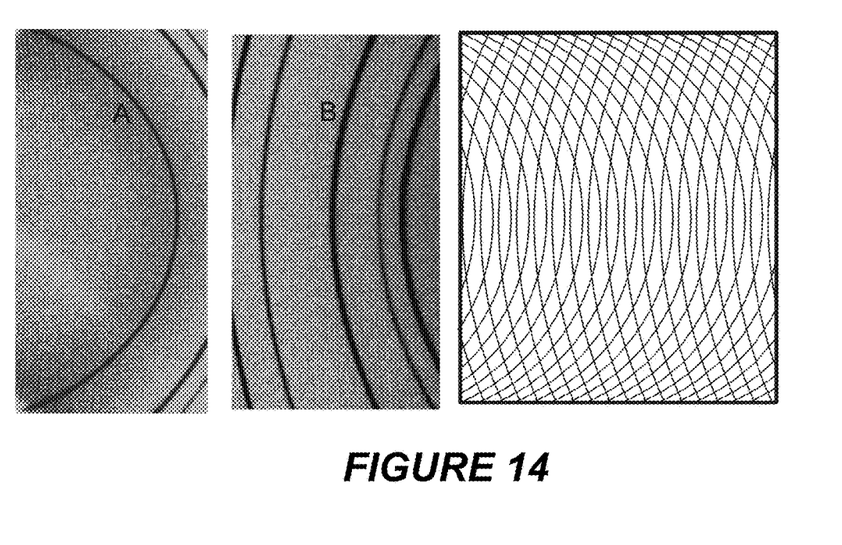
FIG. 14 shows the diffraction rings from a corundum sample collected in reflection mode at a relatively low swing angle and at a relatively high swing angle, and the expected overlap of many such diffraction patterns if taken at different swing angles.

Based on the above principles, calibration methods may be employed to address a variety of different reference patterns that may be generated. For example, with powder samples containing a large d-spacing lattice plane, such as silver behenate, numerous intersection points can be collected at several different swing angles. In FIG. 12, a diffraction pattern collected from silver behenate is shown to the left side of the figure, while the schematic image to the right side of the figure illustrates the intersections created by overlapping three such diffraction patterns collected at three known relative swing angles. In FIG. 13, the left side of the figure shows a single diffraction ring collected from a corundum sample in transmission mode, while the right side illustrates the intersections created by the overlapping of many such diffraction patterns collected at many different relative swing angles. In another example depicted in FIG. 14, the left side of the figure is a partial diffraction ring collected from a corundum sample in reflection mode at a low 2θ angle (<90°), while the central portion of the figure is a pattern collected at a high 2θ angle (>90°) in reflection mode. On the right side of this figure, the intersections created by overlapping multiple rings at both low 2θ angle and high 2θ angle with various swing angles are shown. Those skilled in the art will recognize that, using this principle of the invention, many different arrangements of intersections may be created using various combinations of diffraction rings collected at different angles.

Figure 15:
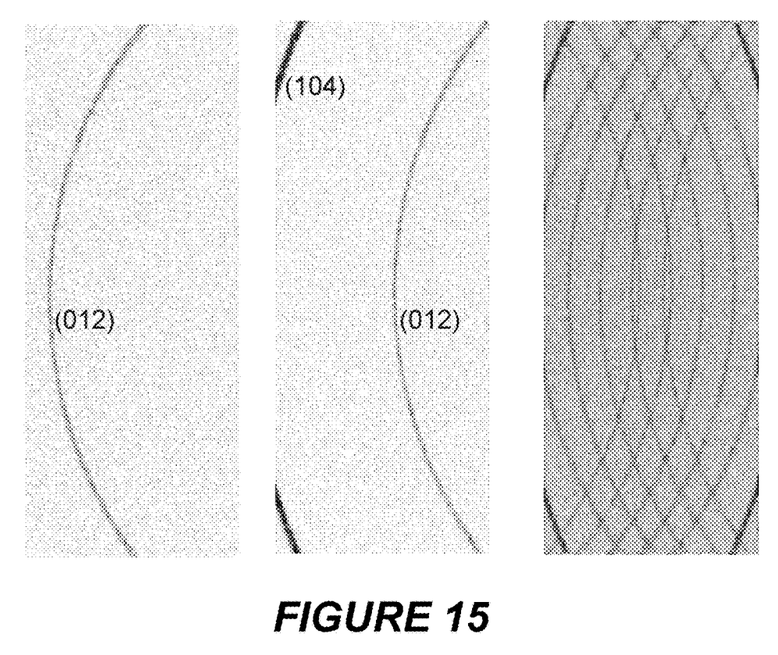
FIG. 15 shows the diffraction rings of diffraction patterns collected at two different swing angles and the overlapping of diffraction patterns at a number of different swing angles.

FIG. 15 shows an experimental example of the intersection grid generated with a PILATUS3 R 100K-A 2D detector (DECTRIS Ltd., Baden-Daettwil, Switzerland) on a corundum sample. The left of the figure shows a 2D frame with the (012) diffraction ring at 2θ=25.60, collected at sample-to-detector distance D=14 cm, Cu Kα radiation, and swing angle α=20°. The middle of the figure shows both of the (012) and (104) rings at swing angle α=26°. A person skilled in the field may choose to use or remove the (104) ring by software for constructing the intersection to avoid confusion. The right of the figure shows the intersection grid generated by overlapping frames collected at ten swing angles of ±18°, ±20°, ±22°, ±24° and ±26°. For a detector without position error, the intersection points coordinates (x,y) can be calculated based on equation (3) to (6) above. The intersection points on the measured frame can be estimated from the diffraction image. The errors between the measured intersection points and the calculated intersection points can then be used to calculate the detector position error. In order to improve the accuracy of the calibration, many intersection grid images can be measured with various diffractions rings at various detector swing angles. A person skilled in the field can expect that the 2D detector calibration based on this invention can use various combinations of frames and procedures, and can also be automated at different levels.

The invention claimed is:

1. A method of determining the spatial orientation of a two-dimensional detector in an X-ray diffractometry system used for detecting X-ray energy diffracted from a sample at a sample location, the method comprising:

locating a polycrystalline material at the sample location;

directing an X-ray beam toward the polycrystalline material such that diffracted X-ray energy is output therefrom;

detecting a first diffraction pattern formed by the diffracted X-ray energy with the detector positioned at a first swing angle defined between the direction of the X-ray beam and a line from a center of a detection surface of the detector to the sample;

detecting a second diffraction pattern formed by the diffracted X-ray energy with the detector positioned at a second swing angle different from the first swing angle; and comparing the detected positions of the first and second diffraction patterns on the detection surface and determining said spatial orientation in response thereto, including locating points of intersection between the first and second diffraction patterns and comparing the relative positions of those intersection points to anticipated relative positions corresponding to a known detector orientation.

2. A method according to claim 1 further comprising detecting at least one additional diffraction pattern formed by the diffracted X-ray energy with the detector positioned at a swing angle different from the first and second swing angles, and comparing the detected positions of all of the diffraction patterns on the detection surface and determining said spatial orientation in response thereto.

3. A method according to claim 1 wherein determining the spatial orientation of the detector comprises determining a rotational orientation of the detector about an axis between a center of the sample and a center of a detection surface of the detector.

4. A method according to claim 1 wherein determining the spatial orientation of the detector comprises determining a rotational orientation of the detector about an axis within a plane of a detection surface of the detector.

5. A method according to claim 4 wherein the axis is a first axis and wherein determining the spatial orientation of the detector further comprises determining a rotational orientation of the detector about a second axis within a plane of a detection surface of the detector that is perpendicular to the first axis.

6. A method according to claim 1 further comprising, after determining said spatial orientation of the detector, making any necessary adjustments thereto as part of a calibration process.

7. A method according to claim 1 further comprising, after determining said spatial orientation of the detector, compensating subsequent diffractometry measurements to correct for deviation of said spatial orientation from a desired orientation.

8. A method of calibrating the spatial orientation of a two-dimensional detector in an X-ray diffractometry system used for detecting X-ray energy diffracted from a sample at a sample location, the method comprising:

locating a polycrystalline material at the sample location;

directing an X-ray beam toward the polycrystalline material such that diffracted X-ray energy is output therefrom;

detecting a plurality of diffraction patterns formed by the diffracted X-ray energy with the detector positioned at a plurality of different swing angles defined between the direction of the X-ray beam and a line from a center of a detection surface of the detector to the sample;

comparing the detected positions of the diffraction patterns on the detection surface and determining said spatial orientation in response thereto, including locating points of intersection between the diffraction patterns and comparing the relative positions of those intersection points to anticipated relative positions corresponding to a known detector orientation; and adjusting the orientation of the detector based on the relative positions of the diffraction patterns so as to reorient the detector to a calibrated position.

9. A method according to claim 8 wherein calibrating the spatial orientation of the detector comprises adjusting a rotational orientation of the detector about an axis between a center of the sample and a center of a detection surface of the detector.

10. A method according to claim 8 wherein calibrating the spatial orientation of the detector comprises adjusting a rotational orientation of the detector about an axis within a plane of a detection surface of the detector.

11. A method according to claim 10 wherein the axis is a first axis and wherein adjusting the spatial orientation of the detector further comprises adjusting a rotational orientation of the detector about a second axis within a plane of a detection surface of the detector that is perpendicular to the first axis.

* * * * *